(12) United States Patent
Koami

(10) Patent No.: US 7,255,441 B1
(45) Date of Patent: Aug. 14, 2007

(54) PUPIL MEASURING DEVICE

(76) Inventor: Elom A. Koami, 438 W. Baker St., St. Paul, MN (US) 55107

( * ) Notice: Subject to any disclaimer, the term of this patent is extended or adjusted under 35 U.S.C. 154(b) by 346 days.

(21) Appl. No.: 11/092,046

(22) Filed: Mar. 30, 2005

(51) Int. Cl.
*A61B 3/10* (2006.01)

(52) U.S. Cl. ..................... 351/218; 351/221
(58) Field of Classification Search .......... 351/218
See application file for complete search history.

(56) References Cited

U.S. PATENT DOCUMENTS

| 2,364,844 | A | | 12/1944 | Fuog |
| 2,371,999 | A | | 3/1945 | Isaacson |
| 2,612,893 | A | | 10/1952 | Engelmann |
| 4,007,980 | A | | 2/1977 | Bracher et al. |
| 4,256,385 | A | * | 3/1981 | Cohen et al. ............... 351/212 |
| 5,599,276 | A | * | 2/1997 | Hauptli et al. .............. 600/112 |
| 5,975,700 | A | | 11/1999 | Koest |
| 6,022,109 | A | | 2/2000 | Dal Santo |
| 6,217,172 | B1 | | 4/2001 | Shibutani et al. |

* cited by examiner

*Primary Examiner*—Jordan Schwartz
*Assistant Examiner*—James C Jones

(57) ABSTRACT

A pupil measuring device includes a portion that is positioned adjacent to a subject's eye and which includes a plurality of concentric circles on a lens as well as an opaque film that moves to cover the circles. Each circle is marked and the film is aligned with the subject's pupil to be circumjacent thereto. The diameter of the pupil can then be read manually or using electronic circuits with the opaque film being used as the indicator of the measurement.

6 Claims, 2 Drawing Sheets

PUPIL MEASURING DEVICE

BACKGROUND OF THE INVENTION

1. Field of the Invention

The present invention relates to the general art of optics, and to the particular field of eye examinations.

2. Description of the Related Art

The size of an individual's pupils is important in neurological and cranial nerve evaluation as well as a fast indication of a brain injury as well as an indication of diseases, such as Alzeheimer's disease or the like and for detecting fatigue, or for detecting alcohol or chemical/substance abuse, or the like and for use in glaucoma screening capability, corneal topography measurement capability, intracranial pressure detection capability, and ocular aberration measurement capability. Furthermore, it is known that the response of an individual's pupil to external light stimulation yields useful information as to the subject's well being. Analysis of an individual's pupil is an effective and non-invasive means of characterizing a subject's brain, nervous and cranial conditions.

Thus, devices for analyzing a subject's pupil may be useful in the medical, transportation, military and law enforcement fields, in industry, and in other areas in which it is desirable to detect such conditions.

The inventor is aware of some devices for performing neurological assessment which include holding a millimeter gauge over the eyes or by subjectively giving a number to the eye diameter. The size of eye pupil is normally equal at rest among a great percentage of individuals. Some individuals are born with unequal pupil size without any underlying pathology. However, the methods known to the inventor are not as accurate as possible.

For some applications, it is desired to monitor the time-response of the individual's pupil as the eye is subjected to various lighting conditions. As an example, such a device would measure the pupil response of a dark-adjusted eye that is subject to a stimulating light pulse (i.e. photostimulus). For such an example, the pupil, initially large due to the dark-adjusted state, will typically decrease in size in response to an external light stimulation flash, and then increase in size upon returning to a dark-adjusted condition.

For example pupilometers are often used in an analysis of a subject. Briefly, conventional pupilometers typically include optical-electronic apparatus for generating a pupillary response-inducing light stimulus, and for measuring the diameter of the stimulated pupil over a period of time to establish the response (including parameters such as pupil constriction velocity, initial, minimum and final pupil diameter, time to minimum, and reflex amplitude) of a user/subject's pupils to the light stimulus. To this end, conventional pupilometers typically include one or more visible light emitting diodes to produce the response-inducing light stimulus (i.e., diodes to generate a visible flash of light directed along an optical path and at the subject's eye to cause contraction of the subject's pupil), and infrared diodes or other IR source and associated optics and electronics adapted to direct the IR source to and from the subject's eye for measuring the dynamic pupillary response to the light stimulus. Some methods and apparatus for measuring pupillary response generally utilize either a pupil imaging technique or a light scattering detection technique.

As can be understood from the foregoing, any analysis of a subject's pupil requires an accurate reading of pupil size.

Some imaging methods and apparatus rely on imaging the eye (or a portion thereof) on a detection device such as charged-coupled device (CCD), or other optical detector array. In these instances, the image of the eye, or a portion thereof, is typically detected on a two-dimensional detection device or a scanning one-dimensional device. The output of the imaging device is processed to determine the size of the pupil or other desired pupillary response data.

Often, especially in emergency situations, such pupil size measurement must be conducted in the field and under adverse conditions. While the inventor is aware of several devices that can analyze a pupil, such as used in pupilometry, the inventor is not aware of any device that can provide rapid and accurate pupil measurements and yet which is also simple and easy to operate.

Therefore, there is a need for an accurate and simple means for reading pupil size.

A further difficulty with many of the techniques known to the inventor is that the technique measures only relative pupil response; the inventor is not aware of methods and apparatus for absolute measurement of the pupil diameter during pupillary response measuring techniques.

Therefore, there is a need for a means for providing an absolute measurement of the pupil diameter.

In addition to the above-mentioned deficiencies in the prior art, there is a lack of practical pupil analysis devices that are cost-effective and relatively simple and compact, and thus suitable for use in portable, hand-held situations.

Therefore, there is a need for a practical pupil analysis device that is cost-effective and relatively simple and compact, and is thus suitable for use in portable, hand-held situations.

PRINCIPAL OBJECTS OF THE INVENTION

It is a main object of the present invention to provide an accurate and simple means for reading pupil size.

It is another object of the present invention to provide a means for providing an absolute measurement of the pupil diameter.

It is another object of the present invention to provide a practical pupil analysis device that is cost-effective and relatively simple and compact, and is thus suitable for use in portable, hand-held situations.

SUMMARY OF THE INVENTION

These, and other, objects are achieved by a hand-held device that includes a plurality of circles and a movable film associated with the circles. The device is located over the subject's pupil and the film is moved to a position adjacent to the subject's pupil. The film can be read manually or by using electronic devices.

Using the pupil measuring device embodying the present invention will permit a health care worker to accurately and quickly measure the size of a subject's pupils. By reading the diameter of a circle aligned with a pupil, the size of a subject's pupil can be accurately determined.

BRIEF DESCRIPTION OF THE DRAWING FIGURES

DETAILED DESCRIPTION OF THE PREFERRED EMBODIMENT

Figure 1:
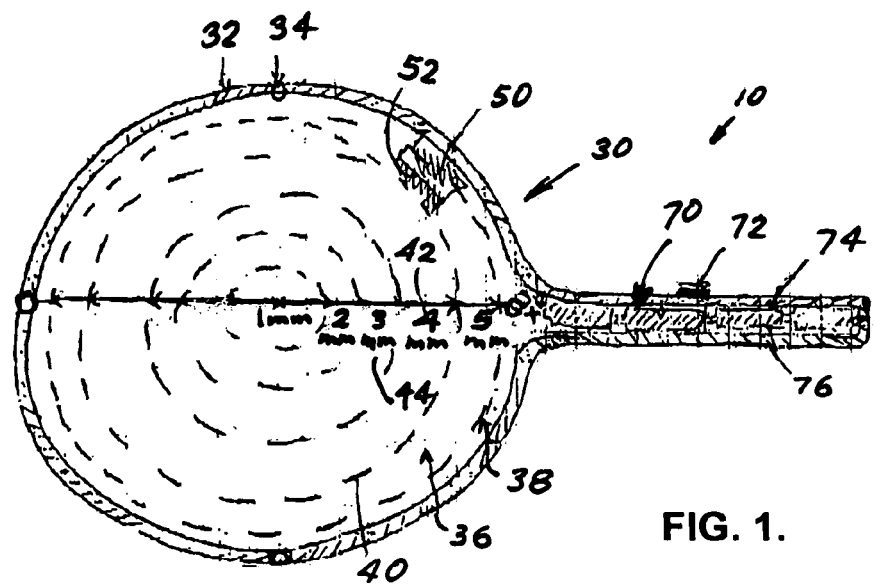
FIG. 1 shows the working end of a pupil measuring device embodying the present invention.
Figure 4:
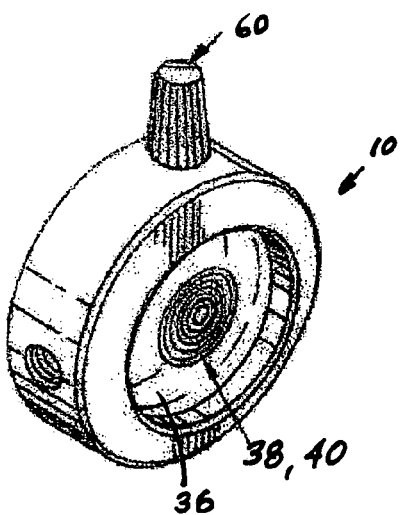
FIG. 4 is a perspective view of the working end of a manually operated version of the device embodying the present invention.
Figure 5:
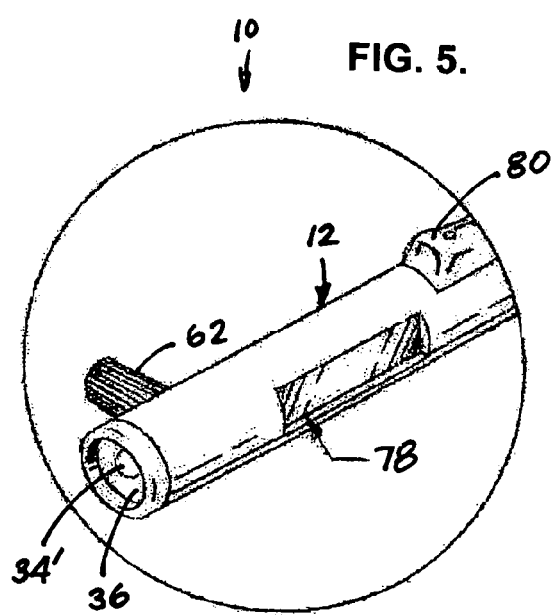
FIG. 5 is a detail view of a readout display used with the pupil measuring device embodying the present invention.
Figure 2:
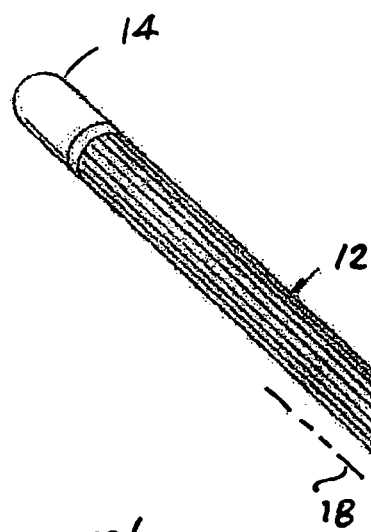
FIG. 2 is a perspective view of a handle used with the pupil measuring device embodying the present invention.
Figure 2:
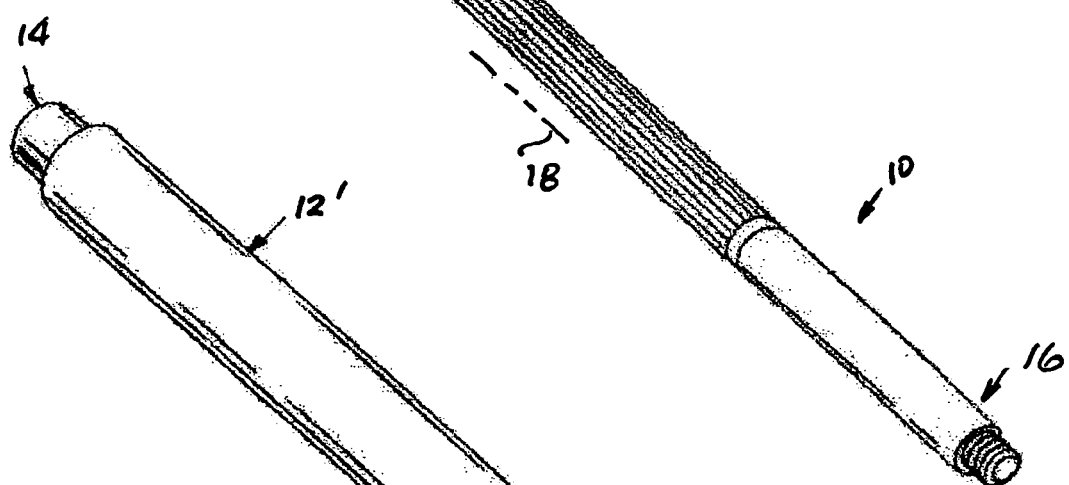

Other objects, features and advantages of the invention will become apparent from a consideration of the following detailed description and the accompanying drawings.

Referring to the Figures, it can be understood that the present invention is embodied in a pupil measuring device 10 which achieves the above-stated objectives.

The pupil measuring device comprises either a manual handle unit 12 or an electronic handle unit 12'. Each of the handle units has a first end 14 which is a distal end when in use, a second end 16 which is a proximal end when in use, and a longitudinal axis 18 which extends between the first end 14 and the second end 16.

Figure 3:
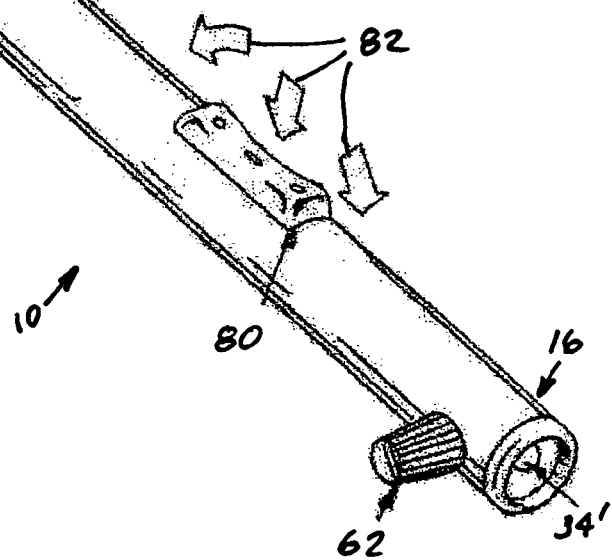
FIG. 3 is a perspective view of a handle used with a manually operated version of the pupil measuring device embodying the present invention.
Figure 1:
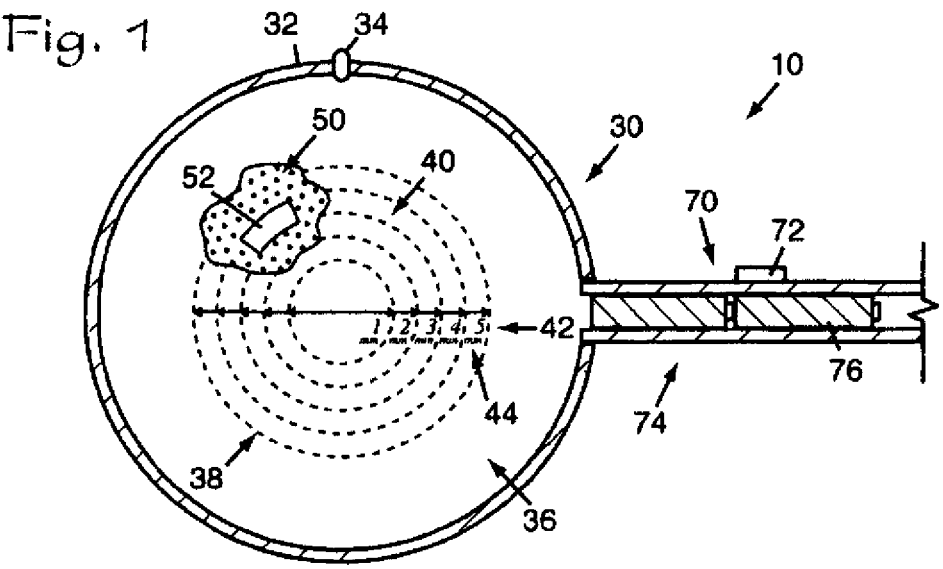
Figure 4:
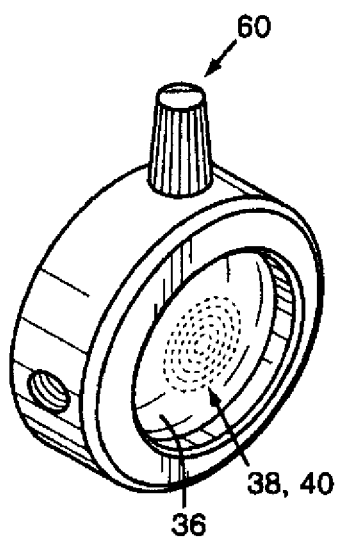
Figure 5:
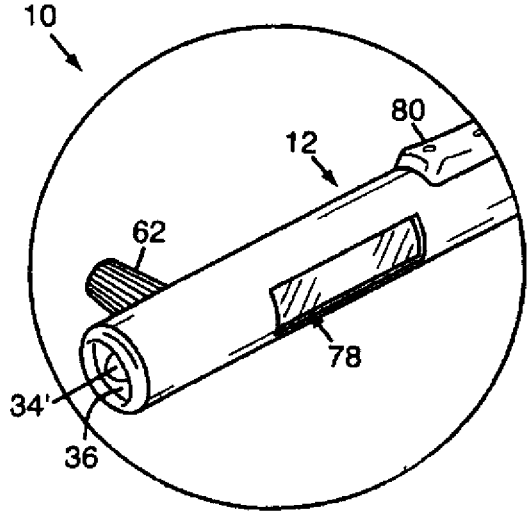

A measuring unit 30 is mounted on the distal end 14 of handle unit 12 and includes a housing 32 and a light-emitting element 34 mounted on the housing 32. In one form of the device 10, the light-emitting element 34 is mounted on the handle as shown in FIG. 3 for light emitting element 34'.

A lens 36 is mounted on the housing 32 and is translucent.

A plurality of concentric circles, such as circles 38 and 40 are defined on the lens 36 and an indicia mark, such as marks 42 and 44, are located on the lens 36 adjacent to each circle.

An opaque film 50 is movably mounted on the lens 36. Opaque film 50 has an opening 52 defined therein and is movable with respect to the lens 36 to locate the opening 52 circumjacent to a selected one of the circles with the opening 52 being located inside the selected circle and the opaque film 50 being located circumjacent to the selected circle such as indicated in FIG. 1 with respect to circle 40.

Means are located in the housing 32 and are connected to the opaque film 50 for moving the opaque film 50. In one form of the device, the means includes knob 60 mounted on the handle, and in another form of the device, the means includes a knob 62 on the handle. In yet another form of the device, the means can include an electrically driven motor located in the handle unit. The exact form of the means for moving the opaque film 50 is not important to the invention and thus will not be discussed in detail.

A light-activating circuit 70 is located in the handle unit and is electrically connected to the light-emitting element 34. Light-activating circuit 70 includes an on/off switch 72 mounted on the handle unit and a power source 74, such as batteries 76, in the handle unit and a readout element 78 connected to the opaque film 50 and mounted on the handle unit.

In one form of the device, the opaque film moving means includes a switch 80 mounted on the handle unit. Switch 80 is electrically connected to the opaque film moving means to move that film 50 in a plurality of directions as indicated by arrows 82 in FIG. 3.

Use of the pupil measuring device can be understood from the teaching of the foregoing disclosure; however, it is noted that the measuring unit 10 is positioned next to a subject's eye and the pupil is located beneath the lens 36. A health care worker will view the pupil through the lens 36 while manipulating the opaque film 50 with respect to the pupil. Once the film 50 is moved to be circumjacent to the pupil, the measurement of the pupil can be made either by electronic means or by simply viewing the indicia on the lens. The movement of the pupil under the influence of light can also be analyzed using the light source if suitable.

It is understood that while certain forms of the present invention have been illustrated and described herein, it is not to be limited to the specific forms or arrangements of parts described and shown.

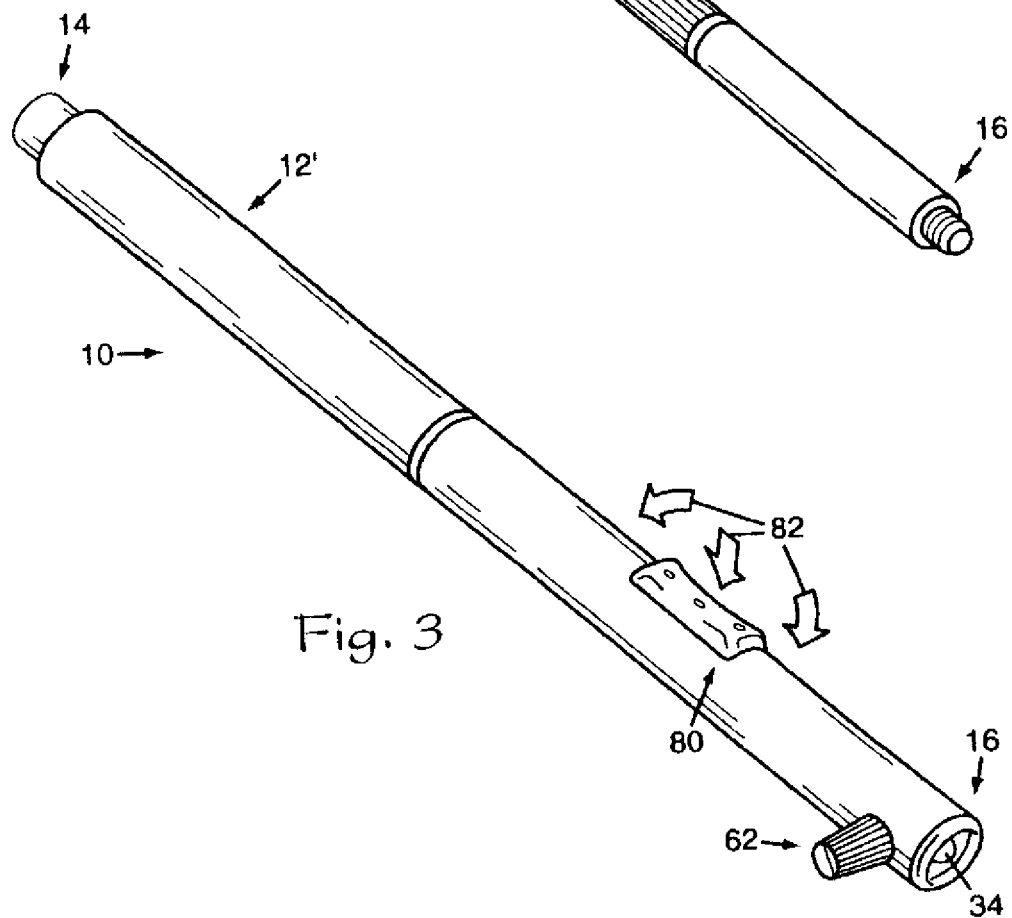

What is claimed and desired to be covered by Letters Patent is:

1. A pupil measuring device comprising:
    a) a handle unit having a first end which is a distal end when in use, a second end which is a proximal end when in use, and a longitudinal axis which extends between the first end and the second end;
    b) a measuring unit mounted on the distal end of said handle and including
        (1) a housing,
        (2) a light emitting element mounted on the housing,
        (3) a lens mounted on the housing,
        (4) a plurality of concentric circles defined on the lens,
        (5) an indicia mark on the lens adjacent to each circle,
        (6) an opaque film movably mounted on the lens, the opaque film having an opening defined therein, the opaque film being movable with respect to the lens to locate the opening circumjacent to a selected one of the circles with the opening being located inside the selected circle and the opaque film being located circumjacent to the selected circle, and
        (7) means in the housing and connected to the opaque film for moving the opaque film;
    c) a light activating circuit located in said handle unit and electrically connected to the light emitting element in said measuring unit, said light activating circuit including
        (1) an on/off switch mounted on said handle unit, and
        (2) a power source in said handle unit; and
    d) a readout element connected to the opaque film and mounted on said handle unit.

2. The pupil measuring device as described in claim 1 wherein said readout element includes a digital readout.

3. The pupil measuring device as described in claim 2 wherein the means for moving the opaque film includes a knob mounted on said handle unit.

4. The pupil measuring device as described in claim 2 wherein the means for moving the opaque film includes a knob mounted on the housing of said measuring unit.

5. The pupil measuring device as described in claim 2 wherein the means for moving the opaque film includes a switch mounted on said handle unit.

6. The pupil measuring device as described in claim 2 wherein the power source of said light activating circuit includes batteries located in said handle unit.

\* \* \* \* \*

UNITED STATES PATENT AND TRADEMARK OFFICE
CERTIFICATE OF CORRECTION

| | | |
|---|---|---|
| PATENT NO. | : 7,255,441 B1 | Page 1 of 4 |
| APPLICATION NO. | : 11/092046 | |
| DATED | : August 14, 2007 | |
| INVENTOR(S) | : Elom Koami | |

It is certified that error appears in the above-identified patent and that said Letters Patent is hereby corrected as shown below:

The title page, should be deleted to appear as per attached title page.

The sheet of drawings consisting of figures 1-5 should be deleted to appear as per attached Figures 1-5.

Signed and Sealed this

Twenty-sixth Day of January, 2010

David J. Kappos
*Director of the United States Patent and Trademark Office*

United States Patent
Koami

(10) Patent No.: US 7,255,441 B1
(45) Date of Patent: Aug. 14, 2007

(54) PUPIL MEASURING DEVICE

(76) Inventor: Elom A. Koami, 438 W. Baker St., St. Paul, MN (US) 55107

( * ) Notice: Subject to any disclaimer, the term of this patent is extended or adjusted under 35 U.S.C. 154(b) by 346 days.

(21) Appl. No.: 11/092,046

(22) Filed: Mar. 30, 2005

(51) Int. Cl.
*A61B 3/10* (2006.01)
(52) U.S. Cl. .................. 351/218; 351/221
(58) Field of Classification Search ........... 351/218
See application file for complete search history.

(56) References Cited

U.S. PATENT DOCUMENTS

| | | | |
|---|---|---|---|
| 2,364,844 A | 12/1944 | Fuog | |
| 2,371,999 A | 3/1945 | Isaacson | |
| 2,612,893 A | 10/1952 | Engelmann | |
| 4,007,980 A | 2/1977 | Bracher et al. | |
| 4,256,385 A * | 3/1981 | Cohen et al. | 351/212 |
| 5,599,276 A * | 2/1997 | Hauptli et al. | 600/112 |
| 5,975,700 A | 11/1999 | Koesi | |
| 6,022,109 A | 2/2000 | Dal Santo | |
| 6,217,172 B1 | 4/2001 | Shibutani et al. | |

* cited by examiner

*Primary Examiner* — Jordan Schwartz
*Assistant Examiner* — James C Jones

(57) ABSTRACT

A pupil measuring device includes a portion that is positioned adjacent to a subject's eye and which includes a plurality of concentric circles on a lens as well as an opaque film that moves to cover the circles. Each circle is marked and the film is aligned with the subject's pupil to be circumjacent thereto. The diameter of the pupil can then be read manually or using electronic circuits with the opaque film being used as the indicator of the measurement.

6 Claims, 2 Drawing Sheets

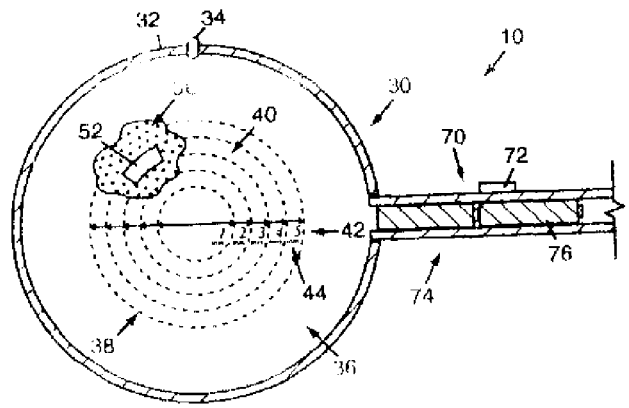

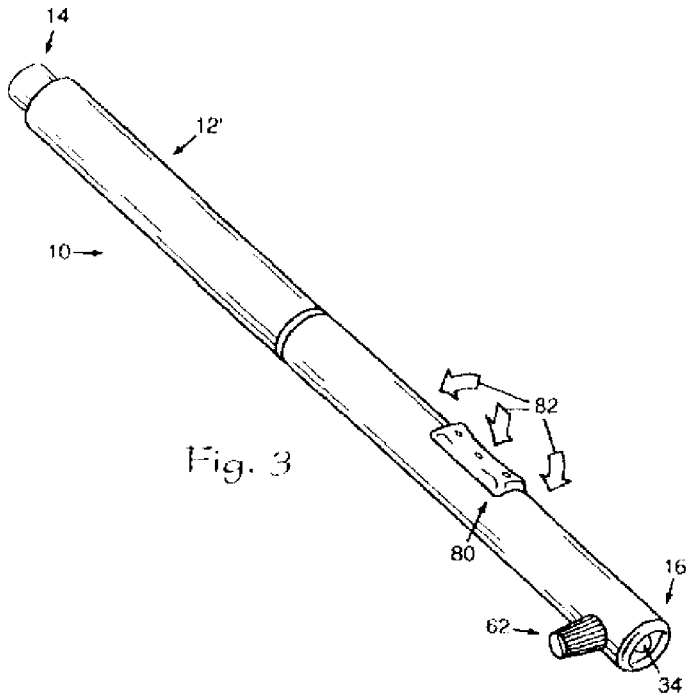

Fig. 3